United States Patent [19]

Fricker

[11] 4,383,040

[45] May 10, 1983

[54] FERMENTATION PROCESS AND APPARATUS

[75] Inventor: Richard Fricker, Derby, England

[73] Assignee: A.G. (Patents) Limited, London, England

[21] Appl. No.: 154,499

[22] Filed: May 29, 1980

[30] Foreign Application Priority Data

Jul. 16, 1979 [GB] United Kingdom ................. 7924754
Mar. 12, 1980 [GB] United Kingdom ................. 8008409

[51] Int. Cl.$^3$ ............................................... C12P 7/06
[52] U.S. Cl. .................................... 435/161; 435/813; 435/316
[58] Field of Search ............... 435/813, 161, 162, 163, 435/164, 165; 426/11, 13

[56] References Cited

U.S. PATENT DOCUMENTS

| | | | |
|---|---|---|---|
| 2,967,107 | 1/1961 | Geiger et al. | 426/11 |
| 3,227,557 | 1/1966 | Ash | 435/813 |
| 3,234,026 | 2/1966 | Coutts | 435/813 |
| 3,729,321 | 10/1970 | Vacano | 426/11 |
| 3,814,003 | 6/1974 | Vacano | 426/11 |

FOREIGN PATENT DOCUMENTS

1087307 10/1967 United Kingdom .

*Primary Examiner*—Raymond N. Jones
*Assistant Examiner*—John Tarcza
*Attorney, Agent, or Firm*—Bernard, Rothwell & Brown

[57] ABSTRACT

A method for continuous fermentation in which carbohydrate solution is fed continuously into a fermentation zone containing substantially homogeneously distributed yeast and carbohydrate solution whereby the carbohydrate is fermented to ethanol, a proportion of the fermenting liquid continuously passing to a pressurised settling tank, yeast depleted liquid being withdrawn from the upper part of the settling tank and yeast enriched liquid being withdrawn from the lower part of said tank and returned to the fermentation zone, a proportion of yeast being withdrawn without being returned to the fermentation zone, said proportion being such that the concentration of yeast in the fermentation zone is substantially constant, and the pressure within the settling tank is sufficient to prevent the formation of gaseous carbon dioxide. The method enables rapid continuous fermentation to take place using high concentrations of yeast. Apparatus for operating the method is described.

9 Claims, 7 Drawing Figures

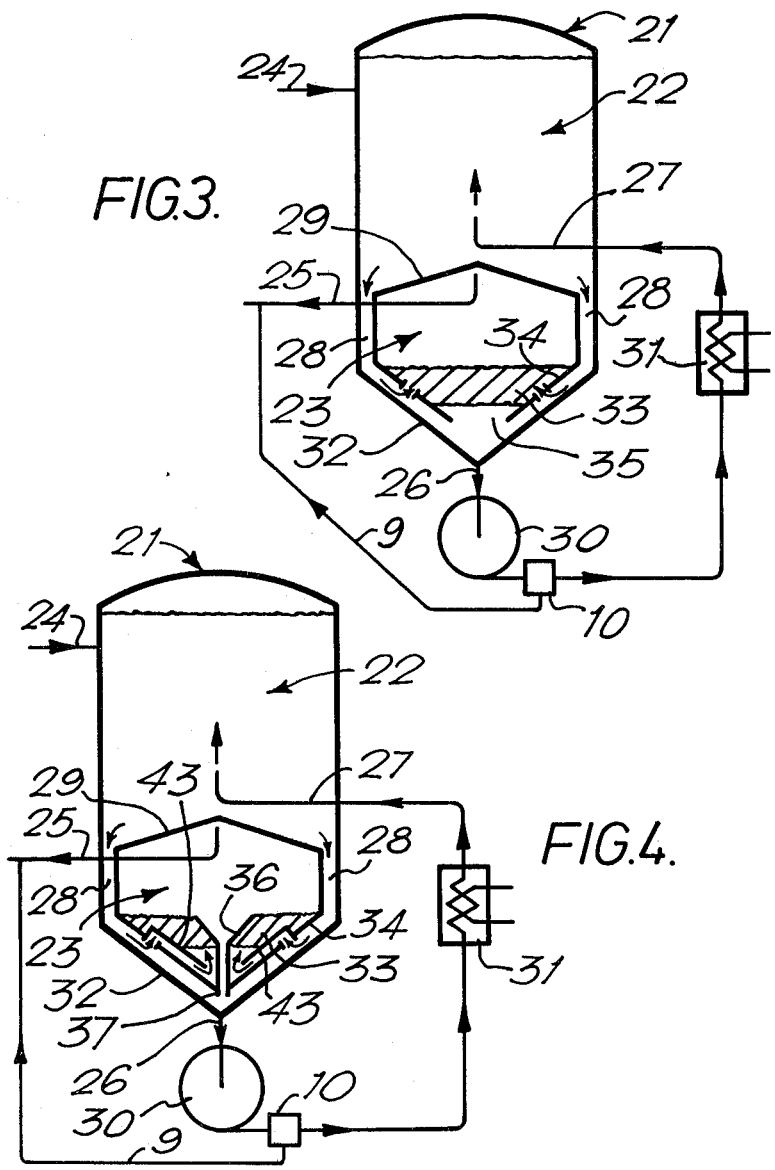

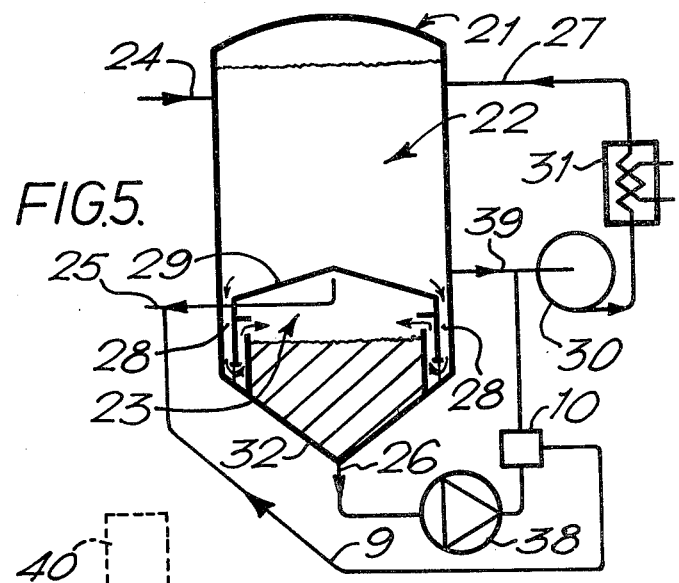
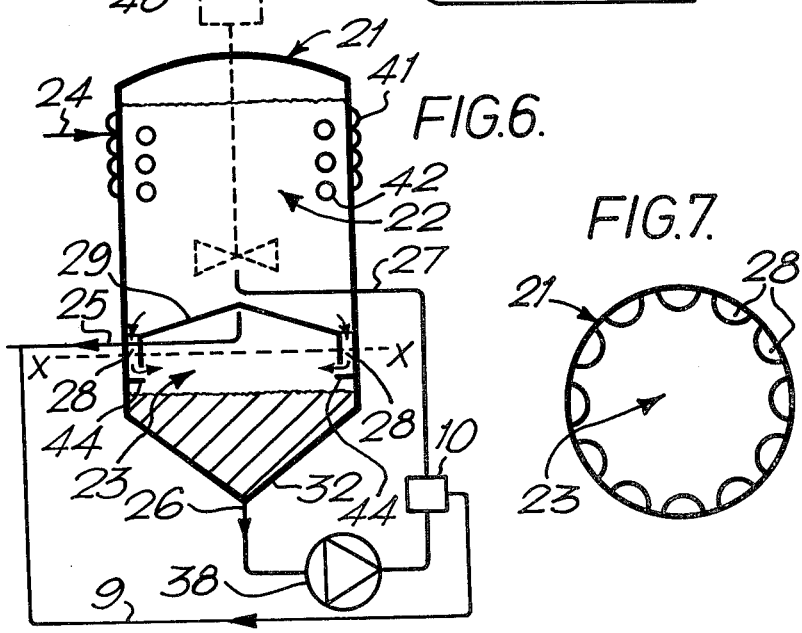

FERMENTATION PROCESS AND APPARATUS

This invention relates to a novel method of continuous fermentation and apparatus therefor.

Continuous fermentation of carbohydrate is, in general, a simpler process than batch fermentation, since it features steady state conditions which are easily maintained by automatic control. For production of aqueous alcohol for distillation, and in particular for the production of industrial alcohol, factors such as flavour and aroma are not significant and there is a demand for a simple, efficient and rapid method of continuous fermentation for this purpose.

A number of methods of continuous fermentation have been proposed; for example the passage of carbohydrate solution through a plug of yeast, through a single stirred tank fermenter or through multifermenter systems in which liquid passes through a series of stirred fermenting vessels. In most such systems, the average alcohol concentration is at a constant, relatively high level, while the average carbohydrate concentration is relatively low. These conditions both militate against high rates of fermentation. This disadvantage can be overcome by maintaining a large body of yeast in the system. This not only increases the rate of fermentation but also serves to improve the efficiency of conversion of carbohydrate to ethanol by suppressing yeast growth. The usual method of increasing yeast concentration is by first separating part of the yeast from the fermented liquid leaving the system and then returning it to the fermentation process. There are however considerable difficulties in carrying out such operations with the high degree of process hygiene which is vital to continuous fermentation and for this reason the return of yeast to continuous fermentation processes has met with little practical success in the past.

We have devised a simple method of rapid continuous fermentation which uses high concentrations of yeast but overcomes some of the previous problems of prior art systems. In our method, a carbohydrate solution is passed through a fermentation zone containing suspended yeast at relatively high concentration, the yeast and carbohydrate in this zone being substantially homogeneously distributed, and a yeast-laden alcohol solution passes to a settling zone from which yeast enriched liquid is returned to the fermenter while yeast depleted liquid is drawn off e.g. to a still. In order to maintain the yeast population in the fermenter substantially constant, some yeast is withdrawn without being returned to the fermentation zone and, most simply, where the alcohol is required for distillation, this yeast is merely passed to the still.

When the yeast concentration in the fermentation zone is maintained at a very high level, rapid sedimentation in the settling zone is essential in order to handle the relatively large volumes of yeast being recycled. Sedimentation rates depend not only on the flocculating characteristics of the yeast but also on the buoyancy created by any bubbles of carbon dioxide trapped on the yeast surface which are generated by the continuation of fermentation in the settling tank. In previous systems using a homogeneous fermentation zone and re-cycling of yeast separated by sedimentation, the settling tank has been operated substantially at atmospheric pressure, and since the solution issuing from the fermentation zone is normally saturated with carbon dioxide, the carbon dioxide generated by further fermentation forms gaseous bubbles. Where relatively small yeast volumes have been concerned, this has not been a serious disadvantage, but in the present system, where high yeast concentrations are envisaged, we have found it necessary to reduce buoyancy to a minimum. The solution we have adopted is to maintain a sufficient pressure in the settling tank to prevent the formation of gaseous carbon dioxide. In general, a pressure of at least about $1.3 \times 10^5$ Nm$^{-2}$ (1.3 bars) e.g. at least $2 \times 10^5$ Nm$^{-2}$ (2 bars) absolute is needed to ensure this.

According to one aspect of the present invention, therefore, there is provided a method of continuous fermentation, in which a carbohydrate solution is fed continuously into a fermentation zone containing substantially homogeneously distributed yeast and carbohydrate solution whereby the carbohydrate is fermented to ethanol, a proportion of the fermenting liquid continuously passing to a pressurised settling tank, yeast depleted liquid being withdrawn from the upper part of the settling tank and yeast enriched liquid being withdrawn from the lower part of said tank and returned to the fermentation zone, a proportion of yeast being withdrawn without being returned to the fermentation zone, said proportion being such that the quantity of yeast in the fermention zone is maintained substantially constant at a desired concentration, and the pressure within the settling vessel being sufficient to prevent the formation of any gaseous carbon dioxide.

According to a further feature of the invention, we provide an apparatus for continuous fermentation comprising a fermentation vessel having a fermentation zone and means for conducting liquid continuously into said zone and out of said zone to a settling tank capable of withstanding an absolute internal pressure of at least about $1.3 \times 10^5$ Nm$^{-2}$ (1.3 bars), means being provided to conduct yeast-enriched liquid from the bottom of the settling tank back to the fermentation zone, there being provided means to lead off yeast-depleted liquid from the top of the settling tank and means to control the quantity of yeast removed without return to the fermentation zone.

The pressure within the settling tank will, in general, be above about $1.3 \times 10^5$ Nm$^{-2}$ (1.3 bars) absolute pressure and will preferably exceed $2 \times 10^5$ Nm$^{-2}$ (2 bars). In that, increased pressures place large stress on the walls of the tank, the pressure will not normally be greater than is strictly necessary to keep carbon dioxide in solution and in general, pressures above about $6 \times 10^5$ Nm$^{-2}$ (6 bars) are not normally required. A pressure of about $4 \times 10^5$ Nm$^{-2}$ (4 bars) is generally sufficient. It will be appreciated that the hydrostatic head of liquid within the settling tank will create somewhat higher pressures at the bottom of the tank than at the top.

The settling tank may be separate from the fermentation vessel or may be situated within the fermentation vessel at a point at which the hydrostatic head of liquid above the tank is sufficient to maintain the desired internal pressure.

Where the settling tank is a separate vessel, the apparatus may comprise a fermentation vessel having an inlet and an outlet spaced from said inlet, a liquid flowline leading from said outlet to a settling tank separate from said fermentation vessel, a liquid flowline leading from the bottom of the settling tank back to the fermentation vessel, there being provided means to move liquid from the fermentation vessel to the settling tank, means to return yeast-enriched liquid from the bottom of the settling tank to the fermentation vessel, means to lead off yeast-enriched liquid from the bottom of the settling tank without returning it to the fermentation vessel, means to lead off yeast-depleted liquid from the top of the settling tank and means to control the quantity of yeast-enriched liquid removed without return to the fermentation vessel.

In general, it is convenient to withdraw all the yeast enriched liquid from the bottom of such a separate settling tank and to divide this by a suitable valve system. The valve positions may, for example, be operated by a cyclic timer to regulate the time for which the yeasty liquid flows along each respective line. The system will be set to maintain the yeast concentration in the fermentation zone at a relatively high level, for example 6-15%, e.g. 10-14% by weight of wet pressed yeast.

Where the fermented product is required for distillation the yeasty liquid which is not recycled can simply be mixed with the yeast depleted liquid for passage to the still. The presence of yeast in the still liquor is not disadvantageous and a proportion of the spent liquid from the still can, indeed, be mixed with the initial carbohydrate solution to provide nutrient material for the fermentation, as well as conserving heat and reducing effluent.

The carbohydrate solution will normally be derived from natural cellulose or starch by enzymic or other hydrolysis or from molasses or other natural sugars. Further nutrients may be present to facilitate optimal performance of the yeast. As indicated above, a proportion of the spent liquid from the still may be added, thereby permitting recycling of unfermented carbohydrate and utilising the nitrogen content of the autolysed yeast. The carbohydrate solution will normally be aerated before entering the fermenter.

In order to promote efficient sedimentation of yeast in the settling tank, yeast activity may be suppressed by lowering the temperature, e.g. to about 10°-15° C. However, this may be unnecessary or even undesirable with some yeasts.

By maintaining a constant high concentration of yeast in the fermentation zone, the rate of fermentation can be high and alcohol thereby produced particularly rapidly. However, removal of heat from the fermentation zone requires particular attention under these circumstances and while the fermentation zone could be provided with a cooling jacket for removal of heat, with internal agitation of the medium to ensure uniform temperature conditions, a more effective method of heat removal is to recirculate medium from the fermentation zone through a heat-exchanger. This technique also serves to agitate the fermentation medium to ensure substantially uniform conditions in the fermentation zone. It is convenient, therefore, to pump yeasty liquid from the fermentation zone through a cooled heat exchanger and back into the fermentation zone. This recirculation loop can advantageously be combined with the system for passing yeasty liquid through the settling tank. Where it is desired to cool the yeasty liquid entering the settling tank to promote sedimentation, it is advantageous to lead a proportion of the medium passing through the recirculation loop from a point downstream of the heat exchanger, through the settling tank and to return the yeast concentrate from the settling tank back into the recirculation loop at a point further downstream. If a constriction is provided in the recirculation loop between the junctions leading to and from the settling tank, the pump recirculating liquid through the recirculating loop may be used to drive liquid through the settling tank. Valves may be used to control the proportion of the recirculating liquid led off through the settling tank. If it is not desired to cool the liquid passing to the settling tank, the junctions leading to and from the settling tank may be upstream of the heat exchanger.

The rate of recirculation through the heat exchanger is determined mainly by the degree of agitation of the fermentation medium which is required. The heat load to be removed is determined by the rate of fermentation, and the inlet temperature of the heat exchanger is that of the fermentation medium in the fermentation zone, which should be maintained at its optimal value by adjusting the rate of coolant flow to the heat exchanger. The outlet temperature of the heat exchanger is thus determined largely by these factors and the size and cooling rate of the heat exchanger. The temperature of the liquid entering the settling vessel may be varied over a small range by adjusting the rate of recirculation; nevertheless the temperature reduction achieved by the heat exchanger is normally quite sufficient to achieve the desired sedimentation of yeast.

Control of pH in the fermentation zone is conveniently effected by introducing acid or alkali into the recycling loop. Similarly, when beginning a new fermentation, yeast from a yeast propagator may also be introduced into the recycling loop.

The cold liquid passing from the settling tank to the still may be used to cool the incoming carbohydrate solution, which may, in some cases, be held at a high temperature, e.g. 82° C., to maintain sterility, down to the fermentation temperature (which will usually be about 30° C.) and will itself be heated e.g. up to about 77° C., thereby saving heat energy required for distillation. Similarly, a proportion of hot spent liquid from the still may, if required, be passed through a heat exchanger to heat the incoming water entering the carbohydrate preparation vessel, which in many cases will be maintained at a high temperature.

Where sedimentation rates are low, the cross-sectional area of the settling tank must be large in order to obtain adequate separation. It is apparent that the combination of requirements for pressure containment and large diameter of the settling vessel can lead to expensive structures.

We have found that these disadvantages may be eliminated by combining the settling tank into the fermentation vessel in such a way that the hydrostatic pressure in the fermentation vessel is used to pressurise the settling tank so that the common walls between the two vessels are not subjected to significant differential pressure and thus carry little or no pressure-induced load. As a result the thickness of the common walls can be substantially reduced with an attendant reduction in fabrication costs.

Thus, as indicated above, in one embodiment of the present invention there is provided apparatus for continuous fermentation of a carbohydrate solution by yeast which comprises a combined fermentation/separation vessel having a fermentation zone wherein fermentation of substantially uniformly distributed yeast and carbohydrate solution may take place, said fermentation zone being situated above a settling zone wherein at least partial separation of fermented liquor from yeast may take place by sedimentation under pressure sufficient to maintain any carbon dioxide present in solution, said fermentation and settling zones being separated one from the other by one or more common walls such that when fermentation is taking place the pressure on said common wall(s) in the settling zone is counteracted by the hydrostatic pressure on the common wall(s) in the fermentation zone, means to allow passage of liquid from the fermentation zone to the settling zone, an inlet for fermentable liquor to the fermentation zone, an outlet for separated fermented liquor from the settling zone, and means for recycling at least a part of the separated yeast from the settling zone to the fermentation zone.

Such an apparatus may be used, in fact, for many continuous fermentation processes, in addition to processes primarily intended for alcohol (ethanol) production (both for potable and non-potable alcohol production) for example in antibiotic production.

In the production of ethanol, the yeast concentration, fermentation and settling temperatures and the pressure in the settling tank may be in the same ranges as indicated above for apparatus using a separate settling tank. Adequate pressure can be achieved if the lead of fermenting liquor above the settling tank is sufficiently great, e.g. about 3 meters or greater, e.g. from 10 meters up to about 25 meters.

The invention will now be described by way of illustration only with respect to the accompanying drawings in which:

FIGS. 2 to 6 show five different embodiments of fermentation apparatus for continuous fermentation according to the invention in diagrammatic form; and FIG. 7 shows a cross-section along the line X—X of the apparatus shown in FIG. 6.

Figure 1:
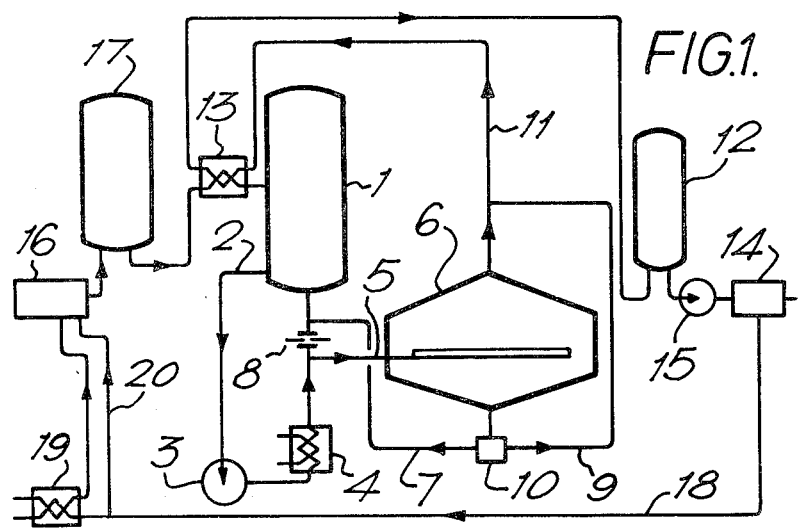
FIG. 1 is a diagrammatic representation of one overall fermentation system according to the invention.

In the system shown in FIG. 1, the fermentation vessel 1 is provided with a recirculating loop 2 including a pump 3 and a heat-exchanger 4. Coolant passing through the heat exchanger serves to cool the recirculating liquid. A line 5 leads to a settling tank 6 and a line 7 leads back to the recirculating loop 2. A constriction 8 in the recirculating loop 2 causes liquid impelled by the pump 3 to pass through the settling tank 6. A line 9 leads from the line 7 via a valve system 10 serving to control the volume ratio of liquid passing along lines 7 and 9 respectively. An alternative position for the valve system would be at the junction of lines 9 and 11. A line 11 leads from the top of the settling tank 6 to fermentation product storage tank 12 via a heat-exchanger 13 from which alcohol solution can pass to the still 14 via a still feed pump 15. The line 9 joins the line 11, so that a proportion of the yeast-enriched liquid from the bottom of the settling tank 6 is mixed with the relatively clear liquid leaving the top of the tank 6. Carbohydrate solution, e.g. hot wort, is prepared in a carbohydrate preparation vessel 16 from where it passes to a storage tank 17 through the heat exchanger 13 to the fermenter 1, thereby being cooled by the relatively cool liquid in the line 9. Aeration may be effected, for example, between the heat exchanger 13 and the fermenter 1. Hot spent liquid from the still 14 is conducted by a line 18 through a heat exchanger 19 to waste; incoming process water passes through the heat exchanger 19 to the carbohydrate preparation vessel 16. A line 20 leads a proportion of the hot spent liquid from the still directly into the vessel 16.

Valves (not shown) are provided where necessary to control the rate of liquid flow.

In the common features of the apparatus illustrated in FIGS. 2 to 6, carbohydrate solution can enter a combined fermentation/settling vessel 21 via a conduit 24. The upper portion of the vessel 21 contains a fermentation zone 22 wherein the fermentable liquor can be fermented by the action of yeast present therein. The lower portion of the vessel 21 contains a settling zone 23 wherein at least partial separation of fermented liquor from yeast can take place. Liquid can pass from zone 22 to zone 23 via the passages 28. After separation of fermented liquor from yeast in zone 23, the separated fermented liquor may be taken off via a conduit 25, and the separated yeast may be removed from the vessel 21 via the conduit 26. The separated yeast may be recycled to the fermentation zone 22 and enter via the conduit 27.

If required, a proportion of the yeast-enriched liquid may be led from the conduit 27 via a conduit 9 to the conduit 25, a valve system 10 serving to control the volume ratio of liquid passing along lines 27 and 9, whereby the yeast population in the fermentation zone can be maintained substantially constant. Alternatively, the valve system 10 could be situated at the junction of lines 9 and 25, while in some cases yeast may be removed by overflow via the conduit 25 as the height of the settled yeast increases with increasing yeast population.

The fermentation zone 22 and the settling zone 23 of the apparatus illustrated in FIGS. 2 to 6 are separated one from the other by the hood-like member 29. When in use, fermented liquor with yeast suspended therein passes from the fermentation zone 22 to the settling zone 23 via the passages 28 and either through holes in the member 29 or under its lower edge, and in the relatively quiescent zone 23 the yeast suspended in the liquor tends to separate under the effect of gravity. Clarified liquor may be removed from the top of the settling zone 23 via the conduit 25. Separated yeast is removed from vessel 21 via conduit 26.

In the apparatus illustrated in FIGS. 2 to 6, in order to suppress liberation of gaseous carbon dioxide, it is generally necessary that the settling zone 23 is at a depth in the vessel 21 such that the hydrostatic pressure of the liquid in the settling zone is sufficient to prevent the evolution of gaseous carbon dioxide therein. In this way the hood member 29 is subjected to very little pressure difference between the two zones 22 and 23 and can be fabricated from relatively light materials.

Figure 2:
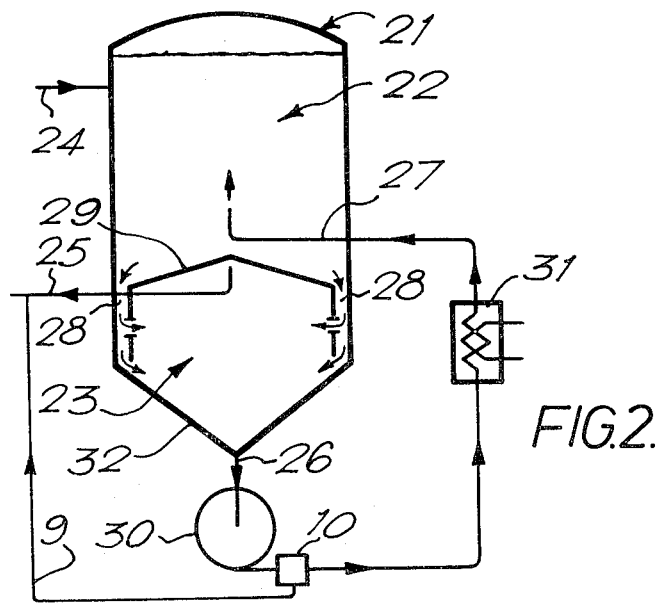

In the embodiments of the apparatus according to the invention shown in FIGS. 2, 3 and 4 the liquid in the fermentation zone may be stirred by recirculation through a pump 30 in order to maintain the yeast in suspension and to ensure a good contact of the fermenting liquid and the yeast. In the apparatus shown in FIGS. 2 to 5 the recirculatory flow may be passed through a heat-exchanger 31 prior to being returned to the fermation zone 22, in order to remove heat of fermentation.

In the apparatus shown in FIG. 2 the hood-like member 29 is dimensioned such that the verical flow velocity of liquid in the settling zone 23 is lower than the sedimentation velocity of the yeast so that only clear liquid is allowed to leave the system via conduit 25. Yeast which sediments in the settling zone 23 falls through a quiescent zone of low flow velocity into a cone-like bottom 32 of vessel 2 from which it is removed by the pump 30 to be recycled to the fermentation zone 22. Liquid leaving the fermentation zone 22 passes downward through the annular passage 28 where flocculation of yeast is promoted prior to its sedimentation in settling zone 23.

In the apparatus illustrated in FIG. 3, a fluidised bed 33 of flocculated yeast is formed in the settling zone 23 through which the liquid from the fermentation zone 22 is caused to flow before leaving the vessel through conduit 25. The purpose of the fluidised bed is to entrap particles of yeast which through their small size and consequent low settling velocity would otherwise pass from the vessel in the separated fermented liquor. The fluidised bed, which operates in a manner analogous to so-called sludge blankets of waste water treatment sedimenters, is contained in a conical extension 34 of the hood-like member 29, where it reaches an equilibrium level according to the upward velocity at average particle size in the bed. Agglomerated yeast leaving the fluidised bed falls through an opening 35 into the cone-like bottom 32 of the vessel 21 and is removed via conduit 26 by pump 30 to be recycled to the fermentation zone 22 through the heat-exchanger 31 and conduit 27.

In the apparatus illustrated in FIG. 4, the settling zone 23 is completely enclosed and an inner cone 36 is present together with a down pipe 37 into which separate yeast from the upper portion of the fluidised zone 33 falls by gravity to the cone-like bottom 32 of vessel 21 and is recycled to the fermentation zone 22 through the pump 30 and heat-exchanger 31. The purpose of the inner cone 36 is to regulate the depth of the fluidised zone 33 within the separation zone 23 and thus to optimise the performance of the apparatus. In this arrangement it is advantageous to create a number of flow conduits 43 passing from the annular passage 28, directing flow to the apex of the cone extension 34. These may conveniently take the form of half pipes welded to the inside of the extension 34. The fermented liquor with yeast suspended therein passes from the fermentation zone 22 to the settling zone 23 via the passages 28, through holes in the conical extension 34 and flow conduits 43 to the underside of the fluidised bed.

FIGS. 2 to 4 described above illustrate apparatus for processes in which the main requirement of the settling zone is for clarification of fermented liquor and in which only very moderate thickening of separated yeast is necessary, since the large pumped recycling flow is capable of entraining a large quantity of a very dilute suspension of separated yeast. In cases where the large recycling flow is not necessary or desired then thickening facilities for separated yeast may be incorporated into the settling zone in order to produce a more concentrated yeast suspension. This may be achieved simply by ensuring that the cross-sectional area of the settling zone is sufficiently large to accommodate the required mass flowrate of solids and that adequate volume is provided for slurry compression as is known in the art.

FIGS. 5 and 6 illustrate apparatus which incorporates means for thickening the separated yeast. FIG. 5 shows an arrangement in which the settling zone 23 shares a common cone-like bottom with the vessel 21. Recirculation of fermenting liquor by pump 30 through a heat-exchanger 31 is effected to remove heat of fermentation and to provide agitation if required. A thickened slurry of separated yeast is withdrawn from the settling zone 23 by slurry pump 38 and then passes to the suction line 39 of pump 30 for incorporation and mixing into the recirculating flow of fermenting liquor. The fermented liquor with suspended yeast passes from the fermentated zone 22 to the settling zone 23 via the passages 28, through holes in the hood-like member 29 and half pipes welded to the inside of member 29.

In FIG. 6 the fermenting liquor in zone 22 may be agitated by the evolution of gaseous by-products of fermentation or by an optical conventional agitator 40. In view of the absence of a heat-exchanger for the recycled yeast it is necessary to extract the heat of fermentation either by a jacket 41 on the vessel 21 and/or by internal coils 42 through which coolant is circulated. In this arrangement it is advantageous to create a number of flow conduits 28 passing downward from the fermentation zone 22 to the settling zone 23 and these may conveniently take the form of half-pipes welded vertically to the internal walls of vessel 21.

Deflector plates 43 are advantageously fitted to prevent downward flow from disturbing the settling process. A plan view of the cross-section of the vessel 21 and conduits 28 is shown in FIG. 7. As in the apparatus of FIG. 5 a thickened slurry of separated yeast forms at the bottom of vessel 21 and this is withdrawn from the vessel by the slurry pump 38. The yeast slurry is thereafter recycled to fermentation zone 22 through conduits 27.

The following Example serves to illustrate the present invention:

EXAMPLE

An apparatus as shown diagrammatically in FIG. 1 was used for the fermentation of sucrose to produce ethanol for distillation using yeast number NCYC955, date of deposit 21 May 1980 at The National Collection of Yeast Cultures, Redhill, Surrey, England.

A molasses solution containing 14% sucrose, to which supplementary phosphate and nitrogen nutrients had been added, was fed at a rate of 600 kg/h to the fermenting vessel (4 m$^3$ liquid capacity) giving a mean residence time of about 7 h. The fermented liquid containing 6.8% by weight ethanol and 0.1% residual sucrose was passed through the settling vessel (1.5 m$^3$ capacity) to produce a substantially yeast free ethanol solution. The underflow from the settling vessel which contained all the separated yeast was divided into two streams, one of which was returned to the fermenter, the other being added to the clarified ethanol solution. The flow ratio of the two streams was controlled by the timed operation of on-off valves in the respective flow lines. The valve timing was adjusted to maintain yeast concentration in the fermenter at about 12% weight wet pressed yeast.

I claim:
1. A method of continuous fermentation comprising:
   (1) continuously feeding a carbohydrate solution into a fermentation zone containing substantially homogeneously distributed yeast and carbohydrate solution whereby the carbohydrate is fermented to ethanol,
   (2) continuously passing a proportion of the termenting liquid from the fermentation zone to a pressurized settling tank, wherein the pressure within the settling tank is sufficient to prevent the formation of any gaseous carbon dioxide,
   (3) withdrawing yeast depleted liquid from the upper part of the settling tank and yeast enriched liquid from the lower part of said tank, and
   (4) returning the proportion of the yeast enriched liquid withdrawn from the lower part of the settling tank to the fermentation zone, said proportion being such that the quantity of yeast in the fermentation zone is maintained substantially constant at a desired concentration.

2. The method of claim 1 wherein the fermentation zone is a vessel.

3. The method of claim 2 wherein the yeast depleted liquid is subjected to distillation.

4. The method of claim 2 or claim 3 wherein the yeast concentration in the fermentation vessel is maintained in the range of 10-14% by weight of wet pressed yeast.

5. The method of claim 2 or claim 3 wherein the carbohydrate solution is derived from natural cellulose or starch or from molasses or other natural sugars.

6. The method of claim 2 or claim 3 in which the fermenting liquid in the fermentation vessel is cooled and agitated by recirculating fermenting liquid from the fermentation vessel through a heat-exchanger and returning the liquid to the fermentation vessel, and the proportion of the fermenting liquid drawn off to the pressurized settling tank is drawn off from the recirculation loop thereby formed and the yeast enriched liquid from the settling tank is returned to said recirculation loop.

7. The method of claim 2 or claim 3 wherein the pressure within the settling tank is at least about $1.3 \times 10^5$ Nm$^{-2}$ absolute.

8. The method of claim 2 or claim 3 wherein the pressure in the settling tank is at least about $2 \times 10^5$ Nm$^{-2}$ absolute.

9. The method of claim 1 wherein the settling tank is situated within a fermentation vessel below a fermentation zone in said vessel, such that the hydrostatic pressure within the fermentation vessel creates the required pressure in the settling tank, while the common walls between the fermentation zone and the settling tank are not subjected to significant differential pressure.

* * * * *